(12) United States Patent
Sharif et al.

(10) Patent No.: US 7,235,556 B2
(45) Date of Patent: Jun. 26, 2007

(54) METHODS OF TREATING DRY EYE DISORDERS

(75) Inventors: Najam A. Sharif, Keller, TX (US); Mark R. Hellberg, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 549 days.

(21) Appl. No.: 10/824,013

(22) Filed: Apr. 14, 2004

(65) Prior Publication Data

US 2004/0209888 A1 Oct. 21, 2004

Related U.S. Application Data

(60) Provisional application No. 60/463,374, filed on Apr. 16, 2003.

(51) Int. Cl.
*A61K 31/50* (2006.01)
(52) U.S. Cl. .................................. 514/252.14; 514/912
(58) Field of Classification Search .................... None
See application file for complete search history.

(56) References Cited

U.S. PATENT DOCUMENTS

| | | | |
|---|---|---|---|
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,744,980 A | 5/1988 | Holly | 424/78 |
| 4,818,537 A | 4/1989 | Guo | 424/427 |
| 4,883,658 A | 11/1989 | Holly | 424/80 |
| 4,914,088 A | 4/1990 | Glonek et al. | 514/76 |
| 4,966,773 A | 10/1990 | Gressel et al. | 424/489 |
| 5,041,434 A | 8/1991 | Lubkin | 514/182 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | MacKeen | 424/602 |
| 5,294,607 A | 3/1994 | Glonek et al. | 514/76 |
| 5,371,108 A | 12/1994 | Korb et al. | 514/762 |
| 5,578,586 A | 11/1996 | Glonek et al. | 514/76 |
| 5,696,166 A | 12/1997 | Yanni et al. | 514/573 |
| 5,800,807 A | 9/1998 | Hu et al. | 424/78.04 |
| 5,958,912 A | 9/1999 | Sullivan | 514/177 |
| 6,153,607 A | 11/2000 | Pflugfelder et al. | 514/178 |
| 6,248,740 B1 | 6/2001 | Kawano et al. | 514/248 |
| 2004/0058875 A1 | 3/2004 | Gamache | 514/15 |

FOREIGN PATENT DOCUMENTS

| | | |
|---|---|---|
| EP | 1 123 936 A1 | 8/2001 |
| EP | 1 243 271 A1 | 9/2002 |
| EP | 1 426 050 A1 | 6/2004 |
| WO | WO 00/03705 | 1/2000 |
| WO | WO 02/48135 A1 | 6/2002 |
| WO | WO 03/053452 A1 | 7/2003 |

OTHER PUBLICATIONS

Fukuda et al., "Inhibition of Allergic Dermal Inflammation by the Novel Imidazopyridazine Derivative TAK-427 in a Guinea Pig Experimental Model of Eczema," *J. of Pharmacology and Exerimental Therapeutics*, vol. 303(3); pp. 1283-1290 (2002).

Lemp et al., "Report of the National Eye Institute/Industry Workship on Clinical Trials in Dry Eyes," *CLAO Journal*, vol. 21(4), pp. 221-231 (1995).

McCulley et al., "Tear Film Structure and Dry Eye," *Contactologia*, vol. 20, pp. 145-149 (1998).

Marsh et al., "Topical Nonpreserved Methylprednisolone Therapy for Keratoconjunctivitis Sicca in Sjogren Syndrome," *Ophthalmology*, vol. 106(4), pp. 811-816 (1999).

Shine et al., "Keratoconjunctivitis Sicca Associated with Meibomian Secretion Polar Lipid Abnormality," *Arch. Ophthalmol.*, vol. 116, pp. 849-852 (1998).

Tauber et al., "A Dose-Ranging Clinical Trial to Assess the Safety and Efficacy of Cyclosporine Ophthalmic Emulsion in Patients with Keratoconjunctivitis Sicca," Lacrimal Gland, Tear Film and Dry Eye Syndromes 2, edited by Sullivan et al., Plenum Press, New York, pp. 969-972 (1998).

Li et al., "Hyperosmolarity Stimulates Producito of MMP-9, IL-kbeta and TNF-alpha by Human Corneal Epithelial Cells via a c-June NH2-terminal Kinase Pathway," Annual Meeting of the Association for Research in Vision and Ophthalmology; Fort Lauderdale, FL, May 5-10, 2002, Abstract No. 1981.

Pflugfelder et al., "Altered cytokine balance in the tear fluid and conjunctiva of patients with Sjögren's syndrome keratoconjunctivitis sicca," *Current Eye Research*, vol. 19 (3), pp. 201-211 (1999).

Pflugfelder, "Antiinflammatory Therpay for Dry Eye," *American J. of Ophthalmology*, vol. 137(2), pp. 337-342 (2004).

*Primary Examiner*—Zohreh Fay
(74) *Attorney, Agent, or Firm*—Patrick M. Ryan

(57) ABSTRACT

Fused pyridazine derivatives are useful for treating dry eye disorders and other disorders requiring the wetting of the eye.

6 Claims, No Drawings

METHODS OF TREATING DRY EYE DISORDERS

This application claims priority to U.S. Provisional Application, U.S. Ser. No. 60/463,374, filed Apr. 16, 2003.

The present invention is directed to the treatment of dry eye disorders. In particular, the present invention is directed to the use of certain fused pyridazine derivatives in the treatment of dry eye and other disorders requiring the wetting of the eye in mammals.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, Report of the National Eye Institute/Industry Workshop on Clinical Trials in Dry Eyes, *The CLAO Journal*, volume 21, number 4, pages 221-231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, Tear film structure and dry eye, *Contactologia*, volume 20(4), pages 145-49 (1998); and Shine and McCulley, Keratoconjunctivitis sicca associated with meibomian secretion polar lipid abnormality, *Archives of Ophthalmology*, volume 116(7), pages 849-52 (1998). Examples of phospholipid compositions for the treatment of dry eye are disclosed in U.S. Pat. Nos. 4,131,651 (Shah et al.), 4,370,325 (Packman), 4,409,205 (Shively), 4,744,980 and 4,883,658 (Holly), 4,914,088 (Glonek), 5,075,104 (Gressel et al.), 5,278,151 (Korb et al.), 5,294,607 (Glonek et al.), 5,371,108 (Korb et al.) and 5,578,586 (Glonek et al.). U.S. Pat. No. 5,174,988 (Mautone et al.) discloses phospholipid drug delivery systems involving phospholipids, propellants and an active substance.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

Aside from efforts directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye conditions in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Some recent literature reports suggest that patients suffering from dry eye syndrome disproportionately exhibit the hallmarks of excessive inflammation in relevant ocular tissues, such as the lacrimal and meibomian glands. The use of various compounds to treat dry eye patients, such as steroids [e.g. U.S. Pat. No. 5,958,912; Marsh, et al., Topical nonpreserved methylprednisolone therapy for keratoconjunctivitis sicca in Sjogren syndrome, *Ophthalmology*, 106 (4): 811-816 (1999); Pflugfelder, et. al. U.S. Pat. No. 6,153,607], cytokine release inhibitors (Yanni, J. M.; et. al. WO 0003705 A1), cyclosporine A [Tauber, *J. Adv. Exp. Med. Biol.* 1998, 438 (Lacrimal Gland, Tear Film, and Dry Eye Syndromes 2), 969], and 15-HETE (Yanni et. al., U.S. Pat. No. 5,696,166), has been disclosed.

Fused pyridazine derivatives, including 2-[6-[[3-[4-(diphenylmethoxy) piperidino]propyl]amino]imidazo[1,2-b]pyridazin-2-yl]2-methylpropionic acid dihydrate ("TAK427"), are disclosed as useful in the treatment or prevention of asthma, allergic conjunctivitis, allergic rhinitis, chronic urticaria or atopic dermatitis in U.S. Pat. No. 6,248,740. TAK-427 is reported to inhibit allergic dermal inflammation in a guinea pig model of eczema. TAK-427 has not been reported to be useful in the topical treatment of dry eye.

SUMMARY OF THE INVENTION

The present invention is directed to methods for the treatment of dry eye and other disorders requiring the wetting of the eye, including symptoms of dry eye associated with refractive surgery such as LASIK surgery. According to the methods of the present invention, certain fused pyridazine derivatives are administered to a patient suffering from dry eye or other disorders requiring wetting of the eye. The fused pyridazine derivatives are preferably administered topically to the eye.

DETAILED DESCRIPTION OF THE INVENTION

According to the present invention, fused pyridazine derivatives of formula (I) are administered to a patient suffering from dry eye.

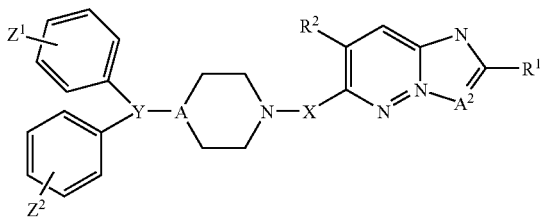

(I)

wherein:
$Z^1$, $Z^2$ independently=H, F, Br, Cl, F, or $C_{1-3}$ alkyl;
Y=CH—(CH2)$_n$ or CH—O;
n=0-3;
A=CH or N, provided that when Y=CH—O then A=CH;
$A^2$=CH or N;
X=(CH2)$_{n'}$Y$^2$ or (CH2)$_{n'}$-Y$^3$(CH2)$_{n''}$Y$^2$;
$X^2$=H, OR$^5$, $C_{1-6}$ alkyl, C(O)OR$^6$, or C(O)N(R$^7$)H;
n'=2-6;
n"=24;
$Y^2$=O, S, or NH
$Y^3$=O or S;
$R^1$=H, or (C(R$^3$)(R$^4$))X$^2$; and
$R^2$, $R^3$, $R^4$, $R^5$, $R^6$, $R^7$ independently=H or $C_{1-6}$ alkyl.

Preferred compounds of formula (I) are those wherein:
$Z^1$, $Z^2$=H
Y=CH—O;
A=CH;
$A^2$=CH or N;
X=(CH2)$_{n'}$Y$^2$;
$X^2$=H or C(O)OR$^6$;
n'=2-4;
$Y^2$=O or NH;
$R^1$=H or (C(R$^3$)(R$^4$))X$^2$; and
$R^2$, $R^3$, $R^4$, $R^6$ independently=H or $C_{1-4}$ alkyl.

Most preferred compounds of formula (I) are those wherein:
$Z^1$, $Z^2$=H;
Y=CH—O;
A=CH;
$A^2$=CH;
X=(CH2)$_{n'}$Y$^2$;
$X^2$=H or C(O)OR$^6$;
n'=2-4;
$Y^2$=O or NH;
$R^1$=(C(R$^3$)(R$^4$))X$^2$
$R^2$, $R^6$ independently=H or $C_{1-4}$ alkyl; and
$R^3$, $R^4$ independently=H or methyl.

Examples of most preferred compounds of formula (I) include:
6-[3-[4-(diphenylmethoxy)piperidino]propylamino][1,2,4]triazolol[1,5,b]-pyridazine;
6-[3-[4-(diphenylmethoxy)piperidino]propylamino]-2-methyl[1,2,4]triazolo[1,5,b]pyridazine;
2-[6-[3-[4-(diphenylmethoxy)piperidino]propylamino]imidazo[1,2,b]pyridazin-2-yl]-2-methylpropionic acid;
2-[6-[3-[4-(diphenylmethoxy)piperidino]propylamino]imidazo[1,2,b]pyridazin-2-yl]-2-methylpropionic acid dihydrate; and
2-[6-[3-[4-(diphenylmethoxy)piperidino]propoxy]imidazo[1,2,b]pyridazin-2-yl]-2-methylpropionic acid.

Compounds of formula (I) can be made by the methods known in the art, including those disclosed in U.S. Pat. No. 6,248,740, the entire contents of which are incorporated herein by reference.

According to the methods of the present invention, a composition comprising one or more of the fused pyridazine derivatives of formula (I) and a pharmaceutically acceptable carrier for topical ophthalmic administration or implantation into the conjunctival sac or anterior chamber of the eye is administered to a mammal in need thereof. The compositions are formulated in accordance with methods known in the art for the particular route of administration desired.

The compositions administered according to the present invention comprise a pharmaceutically effective amount of one or more of the fused pyridazine derivatives of formula (I). As used herein, a "pharmaceutically effective amount" is one which is sufficient to reduce or eliminate signs or symptoms of dry eye or other disorders requiring the wetting of the eye. Generally, for compositions intended to be administered topically to the eye in the form of eye drops or eye ointments, the total amount of the fused pyridazine derivatives of formula (I) will be 0.001 to 1.0% (w/w). When applied as eye drops, 1-2 drops (approximately 20-45 μl each) of such compositions will be administered from once to many times per day.

Preferably, the compositions administered according to the present invention will be formulated as solutions, suspensions and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions.

The compositions administered according to the present invention may also include various other ingredients, including but not limited to surfactants, tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm).

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 6-7.5.

Compositions formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more of the specified cytokine inhibitors. Examples or artificial tears compositions useful as artificial tears carriers include, but are not limited to, commercial products, such as Tears Naturale®, Tears Naturale II®, Tears Naturale Free®, and Bion Tears® (Alcon Laboratories, Inc., Fort Worth, Tex.). Examples of phospholipid carrier formulations include those disclosed in U.S. Pat. Nos. 4,804,539 (Guo et al.), 4,883,658 (Holly), 4,914,088 (Glonek), 5,075,104 (Gressel et al.), 5,278,151 (Korb et al.), 5,294,607 (Glonek et al.), 5,371,108 (Korb et al.), 5,578,586 (Glonek et al.); the foregoing patents are incorporated herein by reference to the extent they disclose phospholipid compositions useful as phospholipid carriers of the present invention.

Other compounds designed to lubricate, "wet," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose, carboxy methylcellulose sodium, hydroxy propylcellulose, dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

A representative eye drop formulation is provided in Example 1 below.

| Example 1 | |
|---|---|
| Compound of formula (I) | 0.001-1.0 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.4 |
| Purified Water | q.s. 100% |

The above composition is prepared by the following method. The batch quantities of boric acid, sodium chloride, disodium edetate, and polyquaternium-1 are weighed and dissolved by stirring in 90% of the batch quantity of purified water. The pH is adjusted to 7.4±0.1 with NaOH and/or HCl. The batch quantity of the fused pyridazine derivatives of formula (I) as a stock solution is measured and added. Purified water is added to q.s. to 100%. The mixture is stirred for five minutes to homogenize and then filtered through a sterilizing filter membrane into a sterile recipient.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A method for the treatment of dry eye which comprises topically administering to the eye of a mammal suffering from dry eye composition comprising a pharmaceutically acceptable carrier and a pharmaceutically effective amount of a compound formula (I)

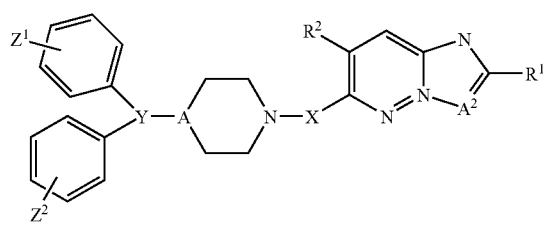

wherein:
$Z^1$, $Z^2$ independently=H, F, Br, Cl, F, or $C_{1-3}$ alkyl;
Y=CH—(CH2)$_n$ or CH—O;
n=0-3;
A=CH or N, provided that when Y=CH—O then A=CH;
$A^2$=CH or N;
X=(CH2)$_{n'}$Y$^2$ or (CH2)$_{n'}$-Y$^3$(CH2)$_{n''}$Y$^2$;
$X^2$=H, OR$^5$, $C_{1-6}$ alkyl, C(O)OR$^6$, or C(O)N(R$^7$)H;
n'=2-6;
n"=2-4;
$Y^2$=O, S, or NH
$Y^3$=O or S;
$R^1$=H, or (C(R$^3$)(R$^4$))X$^2$; and
$R^2$, $R^3$, $R^4$, $R^5$, $R^6$, $R^7$ independently=H or $C_{1-6}$ alkyl.

2. The method of claim 1 wherein
$Z^1$, $Z^2$=H;
Y=CH—O;
A=CH;
X=(CH2)$_{n'}$Y$^2$;
$X^2$=H or C(O)OR$^6$;
n'=2-4;
$Y^2$=O or NH; and
$R^2$, $R^3$, $R^4$, $R^6$ independently=H or $C_{1-4}$ alkyl.

3. The method of claim 2 wherein
$A^2$=CH;

R¹=(C(R³)(R⁴))X²

R², R⁶ independently=H or $C_{1-4}$ alkyl; and

R³, R⁴ independently=H or methyl.

4. The method of claim 1 wherein the compound of formula (I) is selected from the group consisting of
- 6-[3-[4-(diphenylmethoxy)piperidino]propylamino][1,2,4]triazolol[1,5,b]-pyridazine;
- 6-[3-[4-(diphenylmethoxy)piperidino]propylamino]-2-methyl[1,2,4]-triazolo [1,5,b]pyridazine;
- 2-[6-[3-[4-(diphenylmethoxy)piperidino]propylamino]imidazo[1,2,b]-pyridazin-2-yl]-2-methylpropionic acid;
- 2-[6-[3-[4-(diphenylmethoxy)piperidino]propylamino]imidazo[1,2,b]-pyridazin-2-yl]-2-methylpropionic acid dihydrate; and
- 2-[6-[3-[4-(diphenylmethoxy)piperidino]propoxy]imidazo[1,2,b]pyridazin-2-yl]-2-methylpropionic acid.

5. The method of claim 1 wherein the pharmaceutically effective amount of the compound of formula (I) in the composition is 0.001-1.0% (w/w).

6. The method of claim 1 wherein the dry eye associated with refractive surgery.

* * * * *